United States Patent
Miyamoto et al.

(10) Patent No.: US 8,094,912 B2
(45) Date of Patent: Jan. 10, 2012

(54) CARDIAC FUNCTION DISPLAY APPARATUS AND PROGRAM THEREFOR

(75) Inventors: Masaki Miyamoto, Minato-ku (JP); Jun Masumoto, Ichikawa (JP); Masaharu Hirano, Setagaya-ku (JP); Futoshi Sakuragi, Minato-ku (JP)

(73) Assignee: Fujifilm Corporation, Tokyo (JP)

( * ) Notice: Subject to any disclaimer, the term of this patent is extended or adjusted under 35 U.S.C. 154(b) by 297 days.

(21) Appl. No.: 12/531,251

(22) PCT Filed: Mar. 14, 2008

(86) PCT No.: PCT/JP2008/000585
§ 371 (c)(1),
(2), (4) Date: Sep. 14, 2009

(87) PCT Pub. No.: WO2008/111316
PCT Pub. Date: Sep. 18, 2008

(65) Prior Publication Data
US 2010/0074487 A1    Mar. 25, 2010

(30) Foreign Application Priority Data

Mar. 14, 2007  (JP) ................................ 2007-064583

(51) Int. Cl.
*G06K 9/00* (2006.01)
(52) U.S. Cl. ....................................... 382/131
(58) Field of Classification Search .................. 382/128, 382/131, 284, 285; 345/419, 424; 600/410, 600/425
See application file for complete search history.

(56) References Cited

U.S. PATENT DOCUMENTS

| 6,650,927 | B1 | 11/2003 | Keidar |
| 7,286,866 | B2* | 10/2007 | Okerlund et al. ............. 600/407 |
| 7,711,165 | B2* | 5/2010 | Lesage et al. ................. 382/128 |
| 7,822,254 | B2* | 10/2010 | Yatziv et al. .................. 382/131 |
| 2005/0008209 | A1 | 1/2005 | Matsumoto |
| 2005/0093861 | A1 | 5/2005 | Moreau-Gobard |
| 2007/0165952 | A1 | 7/2007 | Goto |

FOREIGN PATENT DOCUMENTS

| JP | 2002-143179 A | 5/2002 |
| JP | 2003-339670 A | 12/2003 |
| JP | 2005-027999 A | 2/2005 |
| JP | 2006-217275 A | 8/2006 |
| WO | 2005/058165 A1 | 6/2005 |

* cited by examiner

*Primary Examiner* — Phuoc Tran
(74) *Attorney, Agent, or Firm* — Sughrue Mion, PLLC

(57) ABSTRACT

Using first voxel data of a three-dimensional medical image obtained by photographing a subject, a functional image representing a function of a heart in at least one position is generated, and using a portion of second voxel data of a three-dimensional medical image obtained by photographing the subject corresponding to an area which includes a blood vessel along an outer myocardial wall of the heart, a morphological image depicting morphology of the blood vessel is generated. Then, the functional image and the morphological image are displayed in a superimposing manner such that at least one position of the heart in the functional image corresponds to at least one position of the heart in the morphological image.

6 Claims, 11 Drawing Sheets

FIG.4
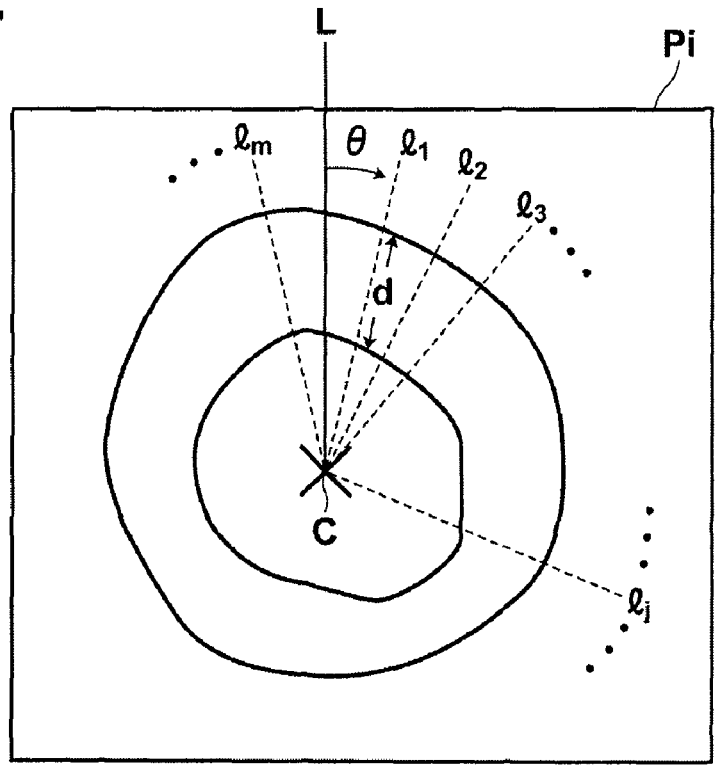
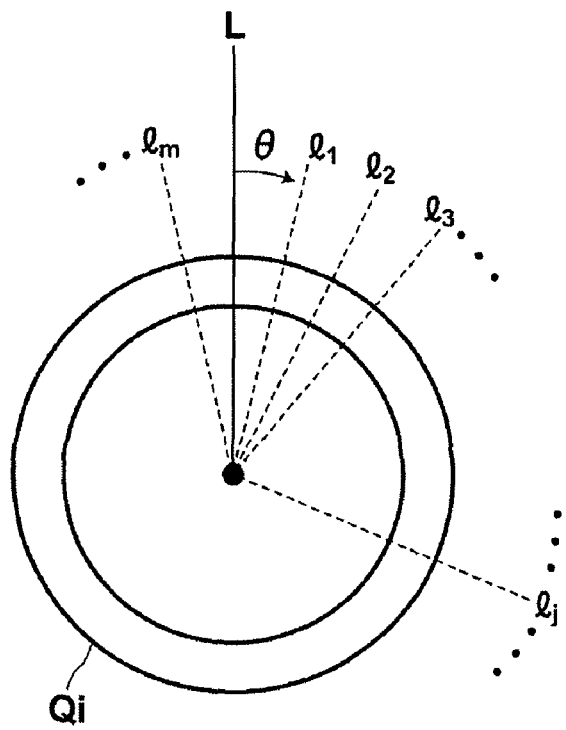

FIG.5
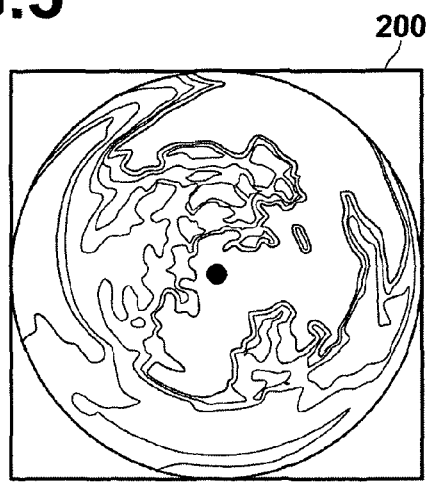
FIG.6A  FIG.6B  FIG.6C
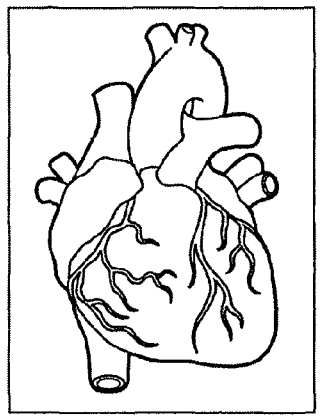 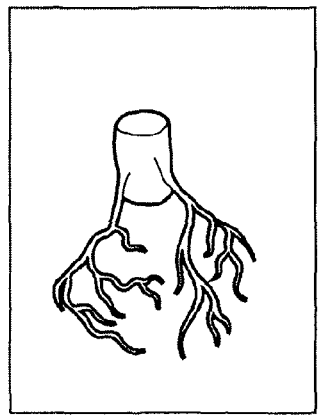 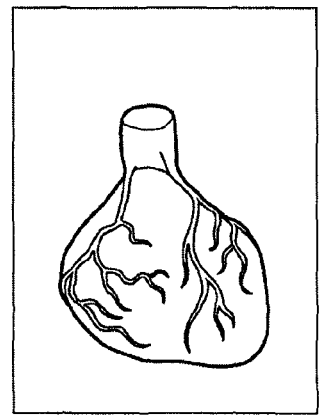

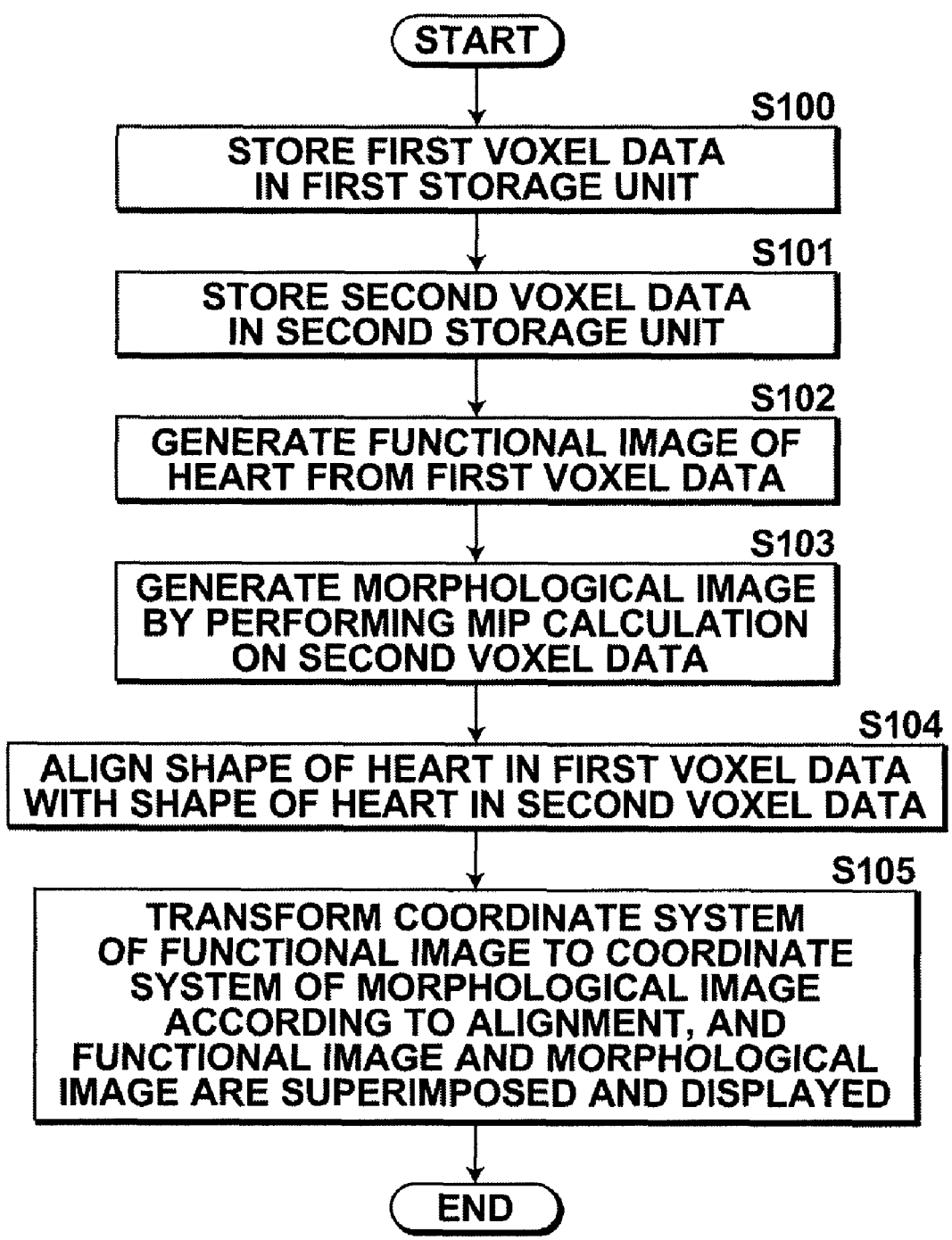

CARDIAC FUNCTION DISPLAY APPARATUS AND PROGRAM THEREFOR

BACKGROUND OF THE INVENTION

1. Field of the Invention

The present invention relates to a cardiac function display apparatus for displaying a function of a heart and a program therefor.

2. Description of the Related Art

Heretofore, as a method for displaying a cardiac function, a bull's eye display method has been used. As illustrated in FIG. 2, the bull's eye display method is a method in which a heart is approximated with an ellipsoid model and images $Q_1$, $Q_2$, - - - $Q_i$, - - - $Q_n$ representing evaluations of the cardiac function on planes $P_1$, $P_2$, - - - $P_i$ - - - $P_n$ provided by slicing the ellipsoid at a regular interval in a direction traversing the major axis of the ellipsoid are concentrically arranged and displayed (FIG. 13). In the bull's eye display method, the function on plane $P_1$ near one of the major vertices of the ellipsoid model is disposed in $Q_1$ located near the center of the concentric circles and the function on plane $P_n$ near the other of the major vertices of the ellipsoid model is disposed in $Q_n$ located outer side of the concentric circles.

This display method is mainly used with functional images. The functional images include images directly photographed by myocardium scintigraphy (SPECT) and images representing functions obtained from analysis results of CT/MRI images.

In the mean time, it has become possible to discover a narrowed section of a blood vessel by injecting a contrast agent into a cardiac blood vessel and geometrically analyzing the state of the vessel with an angiography system or the like. When a narrowed section of a blood vessel is discovered by the angiography system, however, it has not been possible to confirm with the functional image to what extent it has an adverse effect, because the position of the blood vessel and the position of the functional image are not matched. Otherwise, it has not been possible to understand that an abnormal section appearing on the functional image corresponds to which part of the blood vessel.

Consequently, a method that allows observation by relating the state observed on a functional image to the position of a blood vessel is proposed as described, for example, in Japanese Unexamined Patent Publication No. 2005-27999 in which a coronary artery is extracted from three-dimensional image data and a coordinate transformation is performed on the pass of the extracted coronary artery to display the vessel shape in a superimposing manner on the bull's eye functional image.

The method described in Japanese Unexamined Patent Publication No. 2005-27999 in which a line is written on a bull's eye functional image by performing a coordinate transformation on the pass of a coronary artery, however, does not represent the morphology of the blood vessel actually running around the heart, so that it is difficult to determine which part of the coronary artery is observed.

In view of the circumstances described above, it is an object of the present invention to provide a cardiac function display apparatus capable of accurately evaluating the performance of a heart by clearly representing morphology of a blood vessel of the heart. It is a further object of the present invention to provide a computer readable recording medium on which is recorded a program for causing a computer to function as the cardiac function display apparatus.

SUMMARY OF THE INVENTION

A cardiac function display apparatus of the present invention is an apparatus, including:

a functional image generation unit for generating a functional image representing a function of a heart in each position using first voxel data of a three-dimensional medical image obtained by photographing a subject;

a morphological image generation unit for generating, using a portion of second voxel data of a three-dimensional medical image obtained by photographing the subject, which are identical to or different from the first voxel data, corresponding to an area which includes a blood vessel along an outer myocardial wall of the heart, a morphological image depicting morphology of the blood vessel, including a width of the blood vessel, and morphology of a tissue along the outer myocardial wall other than the blood vessel; and a superimpose display unit for displaying the functional image and the morphological image in a superimposing manner such that each position of the heart in the functional image corresponds to each position of the heart in the morphological image.

A computer readable recording medium of the present invention is a medium on which is recorded a program for causing a computer to function as:

a functional image generation unit for generating a functional image representing a function of a heart in each position using first voxel data of a three-dimensional medical image obtained by photographing a subject;

a morphological image generation unit for generating, using a portion of second voxel data of a three-dimensional medical image obtained by photographing the subject, which are identical to or different from the first voxel data, corresponding to an area which includes a blood vessel along an outer myocardial wall of the heart, a morphological image depicting morphology of the blood vessel, including a width of the blood vessel, and morphology of a tissue along the outer myocardial wall other than the blood vessel; and a superimpose display unit for displaying the functional image and the morphological image in a superimposing manner such that each position of the heart in the functional image corresponds to each position of the heart in the morphological image.

The term "a function of a heart in each position" as used herein refers to an operation of the heart in each position. Specific example may be the thickness of the myocardium in each position, that is, a variation in the thickness of the myocardium in the diastolic phase and systolic phase which allows estimation of the operation of the heart in each position. The term "functional image" as used herein refers to an image in which a function of the heart in each position is represented in a visually recognizable manner. More specifically, for example, the display color may be changed according to the function or the function of the heart in each position may be displayed by a numeric value.

The term "morphology" as used herein refers to the appearing shape or state, and the term "morphology of the blood vessel" as used herein refers to the shape or running state of the blood vessel.

Preferably, the functional image is an image in which images representing functions of the heart on a plurality of slice planes cut in a direction traversing a major axis extending from a cardiac base toward a cardiac apex of the heart are arranged concentrically.

Further, preferably, the functional image is an image in which an image representing a function of a slice plane near the cardiac base of the heart is disposed near the center of the concentrically arranged images and an image representing a function of a slice plane closer to the cardiac apex of the heart is disposed in a position farther away from the center.

Still further, the morphological image may be an image generated by performing MIP processing on voxel data present within a predetermined distance from the outer myocardial wall of the heart, which includes the blood vessel along the outer myocardial wall, and a blood vessel present in the predetermined distance is projected in the image.

Still further, the range of the blood vessel on the heart depicted in the morphological image may be wider than the range of the functions of the heart represented by the functional image.

According to the present invention, a functional image representing a function of a heart in each position and a morphological image depicting morphology of a blood vessel are displayed in a superimposing manner such the each position of the heart in the functional image corresponds to each position of the heart in the morphological image, thereby allowing an observation of the heart by relating each function to the anatomical position.

Further, images representing functions of the heart at a plurality of slice planes cut in a direction traversing a major axis extending from the cardiac base toward the cardiac apex of the heart are arranged concentrically, and an image of a slice plane near the cardiac base is disposed near the center of the concentrically arranged images and an image representing a function of a slice plane closer to the cardiac apex of the heart is disposed at a position farther away from the center, whereby a coronary artery of the morphological image displayed in a superimposing manner branches from the center toward the outside, so that an image allowing easy understanding of the anatomical position of the heart may be generated.

Further, generation of a morphological image by performing MIP processing (maximum intensity projection) on voxel data present within a predetermined distance from an outer myocardial wall of the heart which includes a blood vessel along the outer myocardial wall allows an image representing detailed morphology of the blood vessel to be generated and the anatomical position of the heart becomes more understandable.

Still further, the wider range of the blood vessel on the heart depicted in the morphological image than the range of the functions of the heart represented by the functional image may provide a portion in which the anatomical position of the hear can be confirmed without being restricted by the display area of the functional image when the morphological image and functional image are displayed in a superimposing manner, thereby facilitating understanding of the correspondence between the position and function of the heart.

BRIEF DESCRIPTION OF THE DRAWINGS

FIG. 4 is a drawing for explaining the relationship between the thickness of myocardium and bull's eye display.

FIG. 5 shows an example of bull's eye display.

FIG. 6A is a drawing for explaining a method for generating a surface model including a vessel (part 1).

FIG. 6B is a drawing for explaining a method for generating a surface model including a vessel (part 2).

FIG. 6C is a drawing for explaining a method for generating a surface model including a vessel (part 3).

FIG. 10 is a flowchart for explaining an operation of the cardiac function display apparatus of the present invention.

DESCRIPTION OF THE PREFERRED EMBODIMENTS

Figure 1:
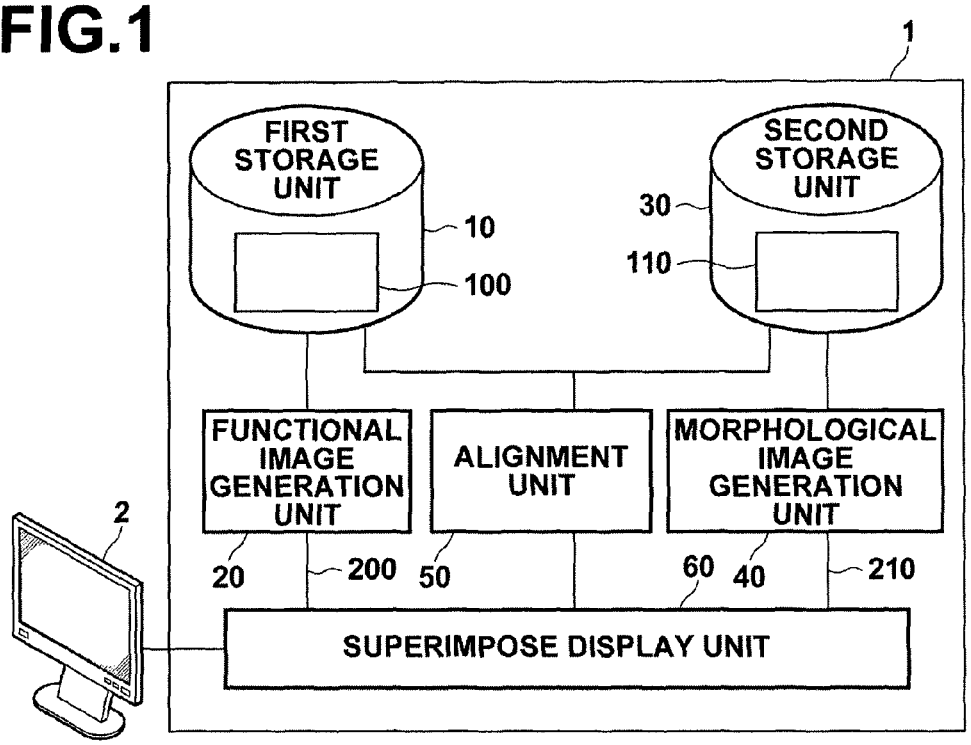
FIG. 1 is a schematic configuration diagram of a cardiac function display apparatus of the present invention.

Hereinafter, an embodiment of the cardiac function display apparatus of the present invention will be described in detail with reference to the accompanying drawings. FIG. 1 is a schematic configuration diagram of the cardiac function display apparatus of the present invention. The configuration of cardiac function display apparatus 1 shown in FIG. 1 is realized by executing a cardiac function display processing program, read in an auxiliary storage device, on a computer. Here, the cardiac function display processing program is stored in recording medium, such as a CD-ROM or the like, or distributed through a network, such as the Internet, and installed on the computer.

Cardiac function display apparatus 1 of the present invention includes first storage unit 10 for storing first voxel data 100 of a three-dimensional medical image obtained by photographing a subject; functional image generation unit 20 for generating functional image 200 representing a function of a heart in each position using voxel data 100; second storage unit 30 for storing second voxel data 110 of a three-dimensional medical image obtained by photographing the subject; morphological image generation unit 40 for generating, using a portion of second voxel data 110 corresponding to an area which includes a blood vessel along an outer myocardial wall of the heart, a morphological image depicting morphology of the blood vessel; alignment unit 50 for aligning the position of first voxel data 100 with the position of second voxel data 110; and superimpose display unit 60 for displaying morphological image 210 and functional image 200 on display unit 2 in a superimposing manner.

First voxel data 100 and second voxel data 110 are data of three-dimensional images obtained by CT (Computed Tomography) or MRI (Magnetic Resonance Imaging). First voxel data 100 are used to generate functional image 200, and second voxel data 110 are used to generate morphological image 210.

Each of first storage unit 10 and second storage unit 30 is a large capacity storage device, such as a hard disk or an image server. They store first voxel data 100 or second voxel data 110 obtained by photographing a subject with a CT or MRI system.

Functional image 200 is an image of distributed evaluation values representing functional evaluations of a heart according to the cardiac movement, diameter of a ventricle, or thickness of the myocardium. Specific examples of functional images include a ventricular diameter image representing the diameter of a ventricle in a certain phase, an end-diastolic ventricular diameter image representing the diameter of the ventricle in a diastolic phase, an end-systolic ventricular diameter image representing the diameter of the ventricle in a systolic phase, a local ejection fraction image representing an ejection fraction of each segmented area, a wall thickness image representing the thickness of the myocardium in a certain phase, an end-diastolic wall thickness image representing a thickness of the myocardium in a diastolic phase, an end-systolic wall thickness image representing a thickness of the myocardium in a systolic phase, a wall thickness variation image representing the difference in thickness of the myocardium from a diastolic phase to a systolic phase, a wall thickness increase rate representing a value of (B−A)/A, in which A indicates a thickness of the myocardium in a diastolic phase, and B indicates the thickness of the myocardium in a systolic phase, a wall movement image representing the difference in ventricular diameter from a diastolic phase to a systolic phase, a myocardial scintigraphic image, and the like.

Functional image 200 representing myocardial scintigraphy is an image of data obtained by injecting a medical agent that concentrates in a myocardium into a subject's arm and externally measuring the distribution of the medical agent. The state of blood flow within the myocardium, metabolism of myocardial tissue, work of the nerves, and the like can be represented by using different medical agents.

When representing the evaluations of cardiac movement by functional image 200, the heart in motion is imaged in a plurality of different phases, then evaluation values of heart function are obtained from the difference between the images, and functional image 200 is generated based on the evaluation values. When the heart is imaged in a plurality of different phases as described above, it is desirable to generate functional image 200 from images obtained by an MRI system, which do not irradiate the subject, in a plurality of different phases.

In the mean time, morphological image 210 is an image representing morphology of a vessel along the surface of an outer myocardial wall of a heart. It is desirable that morphological image 210 be generated from a three-dimensional image obtained by a CT system, in which the structure of each organ is clearly represented.

Preferably, voxel data generated from tomographic images obtained by a CT or MRI system at a fine pitch (e.g., an interval of 3 mm) are used as the second voxel data to be used for generating morphological image 210 in order to finely represent the morphology. On the other hand, when the photographing is required in a plurality of phases according to the movement of a heart in order to generating functional image, there may be a case in which the photographing can not be performed in a plurality of phases if it is performed at a fine pitch. Therefore, voxel data generated from tomographic images obtained by an MRI system or the like at a coarse pitch (e.g., an interval of 5 to 10 mm) are commonly used as the first voxel data.

Functional image generation unit 20 generates functional image 200 from first voxel data 100 stored in first storage unit 10. Here, a detailed description will be made of a case in which cardiac function image 200 representing the wall thickness of a myocardium is generated in bull's eye display method.

Figure 2:
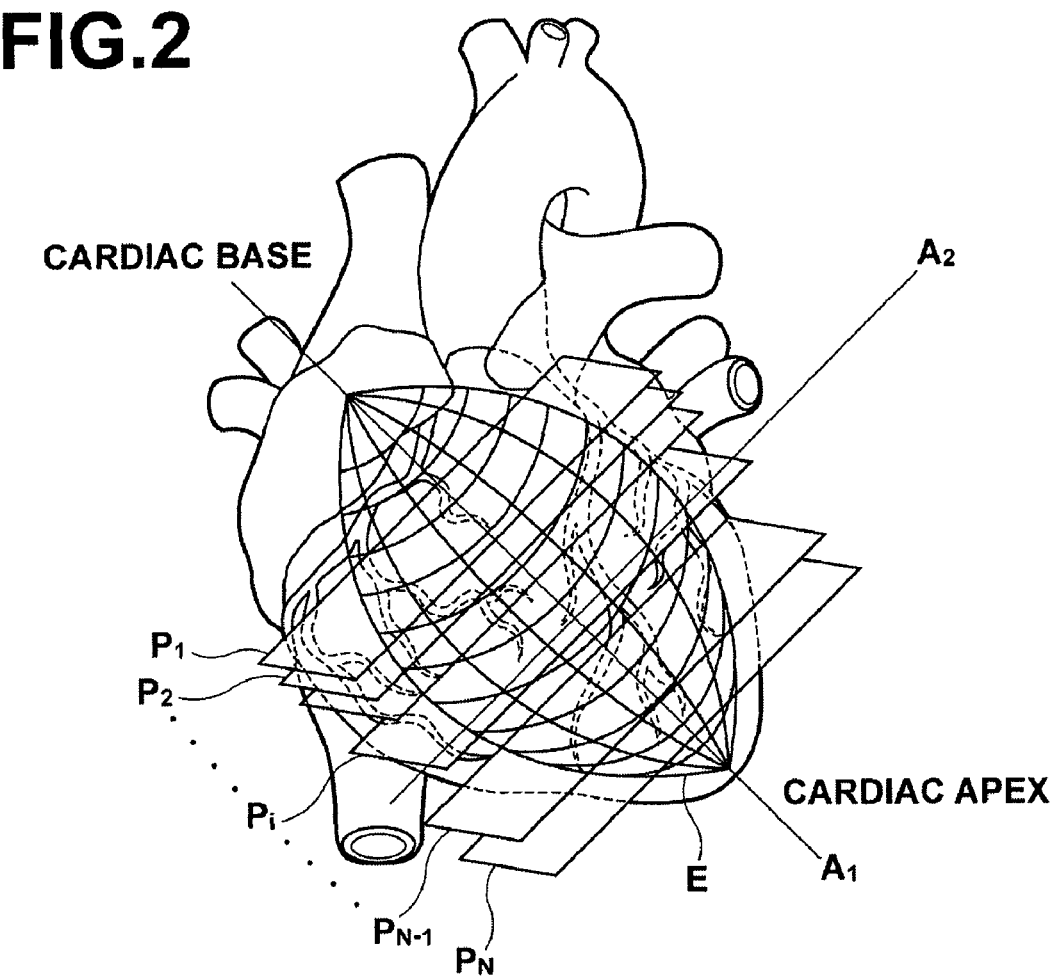
FIG. 2 is a drawing for explaining the relationship between a heart and sliced planes.

First, a surface model is approximated with ellipsoidal shape E shown in FIG. 2 from first voxel data 100, and major axis $A_1$ and minor axis $A_2$ of the heart are determined. Major axis $A_1$ is determined so as to extend from the cardiac base to the cardiac apex of the heart and pass through a central portion of the ventricular area. Minor axis $A_2$ is determined so as to be orthogonal to major axis $A_1$.

Then, cross-sectional images on slice planes $P_1$, $P_2$, $P_i$, - - -, $P_{n-1}$, $P_n$ obtained by cutting the heart in a direction traversing the major axis $A_1$ (direction of minor axis $A_2$) at a regular interval are generated from voxel data 100 and wall thicknesses of the myocardium are obtained. For example, contours of the endocardium and epicardium are extracted from the cross-section on slice plane $P_i$ shown in FIG. 4 and the distance between the contours of the endocardium and epicardium on each of lines $l_2$, $l_2$, $l_3$, - - - $l_j$ - - - $l_m$ is obtained as wall thickness d.

Figure 3:
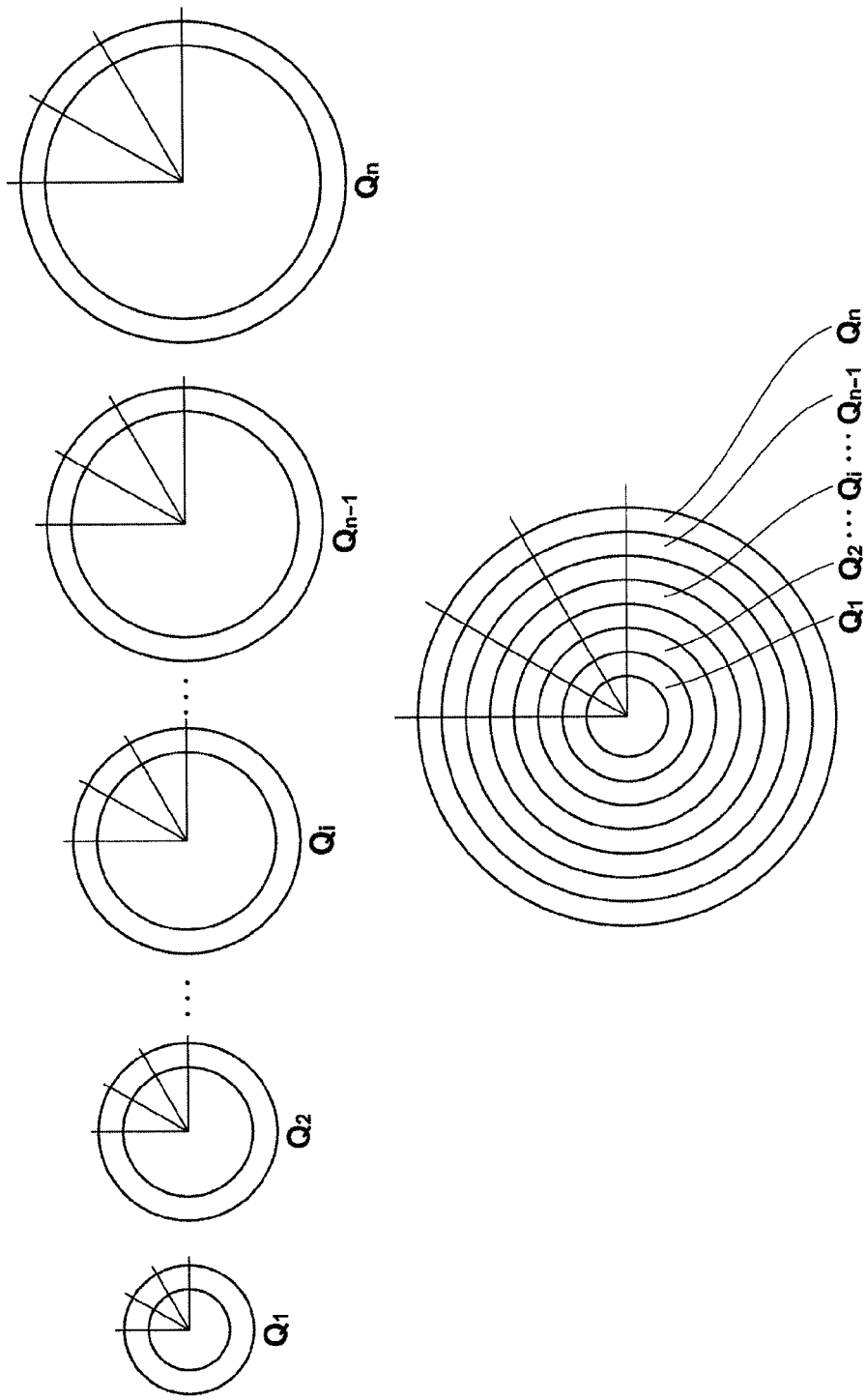
FIG. 3 is a drawing for explaining bull's eye display.

When wall thicknesses of the myocardium are displayed in bull's eye representation, different colors are used according to wall thickness d of the myocardium, and wall thicknesses d on slice planes $P_1$, $P_2$ - - - located near the cardiac base are displayed in concentric circles near the center and wall thicknesses d on slice planes $P_n$, $P_{n-1}$ - - - located near the cardiac apex are displayed in concentric circles on the circumferential side remote from the center. Further, a minor axis image is generated, in which wall thickness d on slice plane Pi is displayed in concentric circle $Q_1$ by relating wall thickness d on each of lines $l_1$, $l_2$, $l_3$ - - - $l_j$, - - - $l_m$ to angle θ between reference line L and each of lines $l_1$, $l_2$, $l_3$ - - - $l_j$, - - - $l_m$. The minor axis image displayed in concentric circles $Q_1$, $Q_2$ - - - $Q_i$, - - - $Q_{n-1}$, $Q_n$ produced in the manner illustrated in FIG. 3 is superimposed to generate functional image 200 in bull's eye representation. FIG. 5 shows an example of wall thicknesses of a myocardium in bull's eye representation. In FIG. 5, each area is an area separated according to wall thickness d. Preferably, each area is displayed with a different color according to the wall thickness d. Otherwise, an arrangement may be adopted in which the thickness of an area is displayed by a numeric value when a mouse or the like is move to the area.

Morphological image generation unit 40 generates morphological image 210 from second voxel data 110 stored in second storage unit 30. In morphological image 210, information of the coronary artery running along the outer myocardial wall is important, and hence a cardiac surface model that includes the coronary artery will be built. First, from a hear having the shape shown in FIG. 6A, the coronary artery running along the outer myocardial wall is extracted (FIG. 6B), and a continuous curved surface is estimated by interpolating between core lines or applying a spline function or the like, whereby a surface model is built. An example of generated surface model is shown in FIG. 6C. Further, with reference to the surface model, a surface model is approximated with ellipsoidal shape E shown in FIG. 2, as in functional image generation unit 20, and the directions of major axis $A_1$ and minor axis $A_2$ of the heart are determined.

Figure 7A:
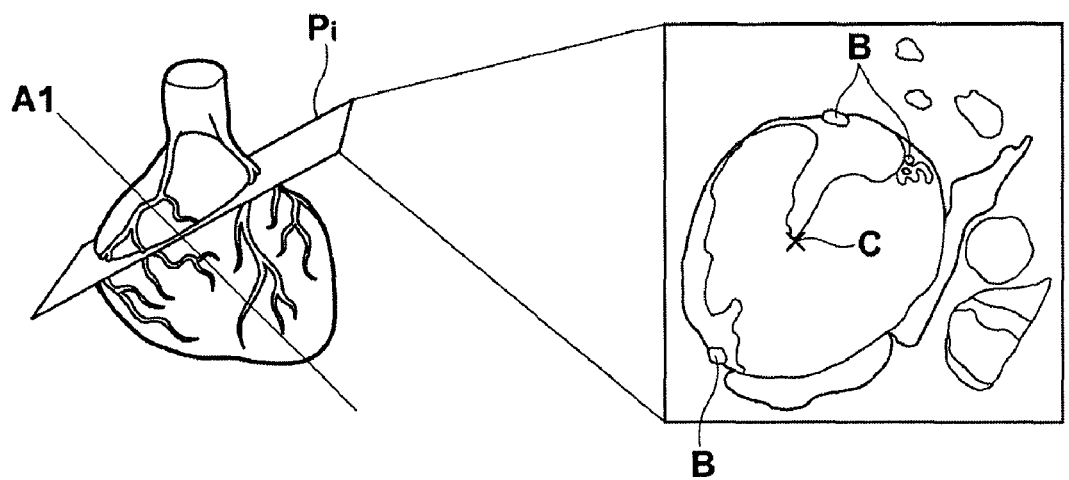
FIG. 7A is a drawing for explaining a method for generating a morphological image (part 1).
Figure 7B:
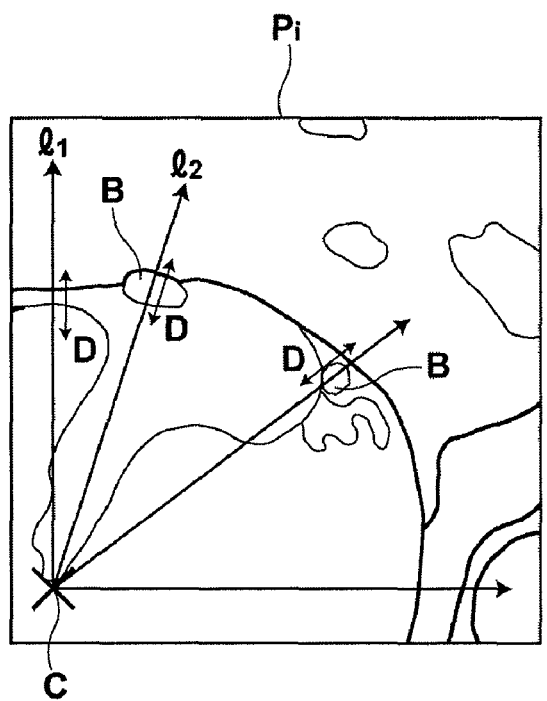
FIG. 7B is a drawing for explaining a method for generating a morphological image (part 2).
Figure 8:
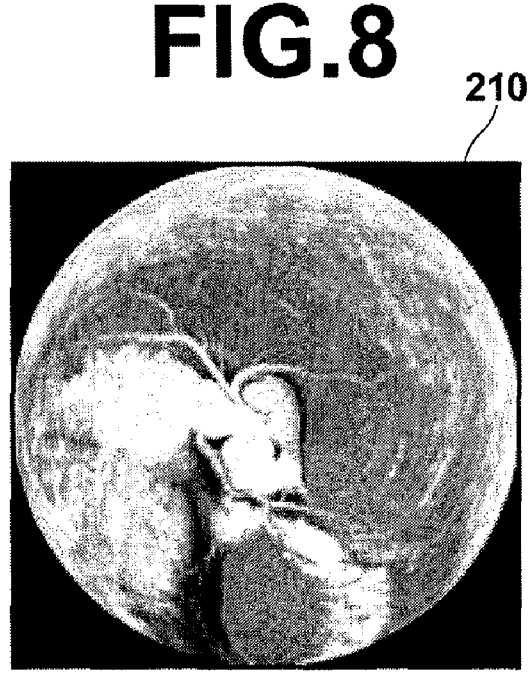
FIG. 8 shows an example of morphological image.

As illustrated in FIG. 7A, slice plane $P_i$ traversing major axis $A_1$ is generated. As a blood vessel has a large pixel value, it can be projected by performing MIP processing on voxel data including the blood vessel. Thus, as illustrated in FIGS. 7A and 7B (which is a partially enlarged view of FIG. 7A), MIP processing is performed using voxel data present within certain distance D in which the lines radially extending to each direction from the center C (where the slice plane intersects major axis $A_1$) of slice image $P_i$ intersects the surface model. Then, a maximum pixel value (hereinafter, MIP value) obtained by searching within distance D of each of lines $l_1$, $l_2$, $l_3, \text{---} l_j, \text{---}, l_m$ by MIP processing is projected to provide bull's eye representation. Distance D is determined based on the diameter of blood vessel B obtained when extracted so that a blood vessel structure is obtained. The running states of a blood vessel along the outer myocardial wall, such as a coronary artery, can be observed in detail by providing slice planes $P_1, P_2, \text{---}, P_i, \text{---}, P_{n-1}, P_n$ with an interval as small as possible and then performing MIP processing. If MIP values of slice planes $P_1, P_2, \text{---}$ near the cardiac base are displayed in concentric circles near the center and MIP values of slice planes $P_n, P_{n-1}, \text{---}$ near the cardiac apex are displayed in concentric circles on the circumferential side remote from the center, branches of the coronary artery along the outer myocardial wall are branched from the center of the concentric circles toward the outside, as shown in FIG. 8, so that the coronary artery running from the cardiac base toward the cardiac apex along the outer myocardial wall can be observed more easily. Further, the use of MIP processing allows the morphology of a blood vessel to be represented finely.

Alignment unit 50 aligns the position of a heart of first voxel data 100 with the position of a heart of second voxel data 110. For example, when first voxel data 100 represent an image of a heart obtained by a MRI system while second voxel data 110 represent an image of the heart obtained by a CT system, it is difficult to position the heart at exactly the same position in the two different images even though the same subject is photographed. Consequently, in order to project morphology of a blood vessel present around the heart at the position of the corresponding heart of functional image 200, the position of the heart shape of first voxel data 100 is aligned with the position of the heart shape of second voxel data 110.

The alignment may be implemented by various types of so-called registration. Here, an example case in which point $x_A$ in image A of first voxel data 100 is transformed to point $x_R$ in image R of second voxel data 110 will be discussed in detail.

If the transform function used is assumed to be T, T can be expressed as follows.

$$T: x_A \to x_R$$

$$T(x_A) = x_R \quad (1)$$

If a heart is regarded as a rigid body, the transform function can be expressed by movements $(t_x, t_y, t_z)$ in X, Y, and Z axis directions in a three-dimensional space and rotations $(\alpha, \beta, \gamma)$ of the axes as shown below.

$$T = \begin{pmatrix} \cos\beta\cos\gamma & \cos\alpha\cos\gamma + \sin\alpha\sin\beta\cos\gamma & \sin\alpha\sin\gamma - \cos\alpha\sin\beta\cos\gamma & t_x \\ -\cos\beta\sin\gamma & \cos\alpha\cos\gamma - \sin\alpha\sin\beta\sin\gamma & \sin\alpha\cos\gamma + \cos\alpha\sin\beta\sin\gamma & t_y \\ \sin\beta & -\sin\alpha\cos\beta & \cos\alpha\cos\beta & t_z \\ 0 & 0 & 0 & 1 \end{pmatrix} \quad (2)$$

When a heart is regarded as a non-rigid body, the shape of the heart varies, the degree of freedom is increased and T is expressed by a complicated function which includes a polynomial equation or a spline function.

More specifically, the transform function may be obtained by detecting a certain number (e.g., three) of anatomical points representing characteristics of a heart. Alternatively, the transform function may be obtained by determining the contour of one image and repeating fitting such that the distance of a point sequence corresponding to the surface of another image becomes the smallest. Otherwise, the transform function may be obtained in a superimposed manner by examining the similarity using the pixel value of each voxel in images. The use of each pixel value in images may cancel out noise component of the pixel so that relatively stable results may be obtained (for example, Japanese Journal of Radiology, Vol. 53, No. 1, PP 60 to 65, January, 2003).

The alignment may be implemented by any of the registration methods described above. Here, for example, the alignment is implemented by regarding the heart as a rigid body and performing evaluation using a correlation coefficient calculated from first and second voxel data 100, 110, and obtaining amounts of displacement, such as rotations and movements, when performing transformation from the coordinate system of the morphological image to that of the functional image.

Figure 9:
FIG. 9 shows an example of image including a morphological image and a functional image superimposed on top of each other (part 1).

Superimpose display unit 60 displays functional image 200 shown in FIG. 5 and morphological image 210 shown in FIG. 8 by superimposing morphological image 210 on functional image 200. Morphological image 210 is superimposed on functional image 200 such that the position of the heart in functional image 200 corresponds to the position of the heart in morphological image 210 using the amounts of displacement obtained by alignment unit 50 when transforming from the coordinate system of the morphological image to the coordinate system of the functional image. FIG. 9 shows an example of superimposed display of functional image 200 shown in FIG. 5 and morphological image shown in FIG. 8. As shown in FIG. 9, the superimposed display allows the observation of which function of the heart is normal or abnormal based on the position of the blood vessel. Further, by placing images located near the cardiac base near the center of the concentric circles and images located near the cardiac apex on the outer side of the concentric circles, the coronary artery branches from the cardiac base toward the cardiac apex, so that the running state becomes more recognizable, whereby understanding of the state of heart function at an anatomical position and each position is facilitated.

Next, a processing flow when an image in which morphological image 210 is superimposed on functional image 200 is displayed using cardiac function display apparatus 1 will be described according to the flowchart of FIG. 10.

First, the heart of a subject is imaged by a CT system and the image is stored in first storage unit 10 as first voxel data 100 (S100). Further, an image of the same subject obtained by a MRI system is stored in second storage unit 20 as second voxel data 110 (S101).

Functional image 200 in which the function of the heart is displayed in bull's eye representation is generated from first voxel data 100 by functional image generation unit 20 (S102).

Next, using second voxel data 110, morphological image 210 is generated by morphological image generation unit 40. A MIP calculation is performed using voxel data including a blood vessel within a certain distance D on each of lines $l_1, l_2, l_3, \text{---}, l_m$ radially extending from a point where the major axis intersects with each slice plane, and morphological image 210 in bull's eye representation is generated by projecting MIP values obtain by the MIP calculation (S103).

The position of the heart in first voxel data is aligned with the position of the heart in second voxel data by alignment unit 50. More specifically, for example, the heart may be evaluated using a correlation coefficient calculated from voxel data 100 and voxel data 110 by regarding the heart as a rigid body and amounts of displacement, such as rotations and movements, when performing transformation from the coordinate system of the morphological image to that of the functional image may be obtained (S104).

Then, by superimpose display unit 60, the coordinate system of functional image 200 is transformed to the coordinate system of morphological image 210 such that the position of the heart in functional image corresponds to the position of the heart in morphological image using the amounts of displacement obtained by alignment unit 50, and functional image 200 and morphological image 210 are superimposed on top of each other and displayed (S105).

Although the description has been made of a case in which the first and second voxel data are different, but the same voxel data may be used. When the same voxel data are used, the alignment is not required.

Where the first voxel data and the second voxel data are those obtained by a CT system and a MRI system respectively or those obtained both by a CT system or a MRI system but with different slice intervals, the alignment is implemented using the registration methods described above. When myocardium scintigraphy is used, however, the alignment may not be successfully implemented by a registration method using correlation between pixels, because the purposes of the images are different and the relationship between the morphological image and the functional image is small. Consequently, in such a case, characteristic points may be selected from each image and a registration may be performed between the points to calculate the amounts of rotation and movement.

Further, although the description has been made of a case in which the coordinate system of functional image 200 is transformed to the coordinate system of morphological image 210. But the coordinate system of morphological image 210 may be transformed to the coordinate system of functional image 200 or both coordinate systems may be changed if the transformation or the changes are performed such that each position of the heart is aligned.

Alternatively, either functional image 200 or morphological image 210 may be generated first, and then the other image may be written on the corresponding positions of the generated image using the alignment information.

Figure 11A:
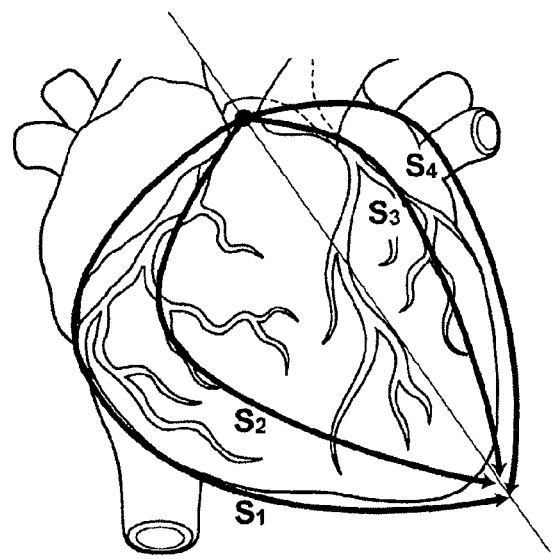
FIG. 11A is a drawing for explaining a method for implementing a bull's eye display according to the distance of lines radially extending along the surface of a heart (part 1).
Figure 11B:
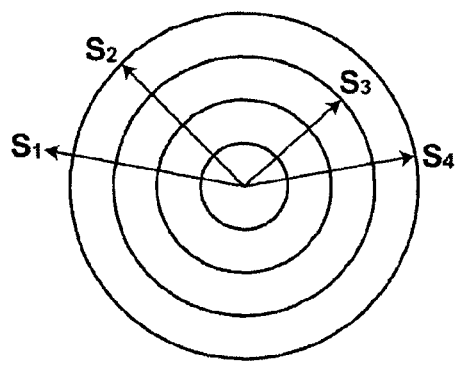
FIG. 11B is a drawing for explaining a method for implementing a bull's eye display according to the distance of lines radially extending along the surface of a heart (part 2).
Figure 12:
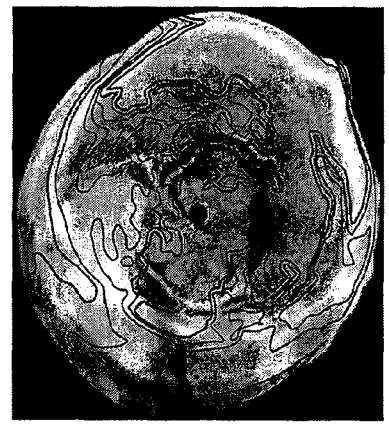
FIG. 12 shows an example of bull's eye display according to the distance of radially extending lines.
Figure 13:
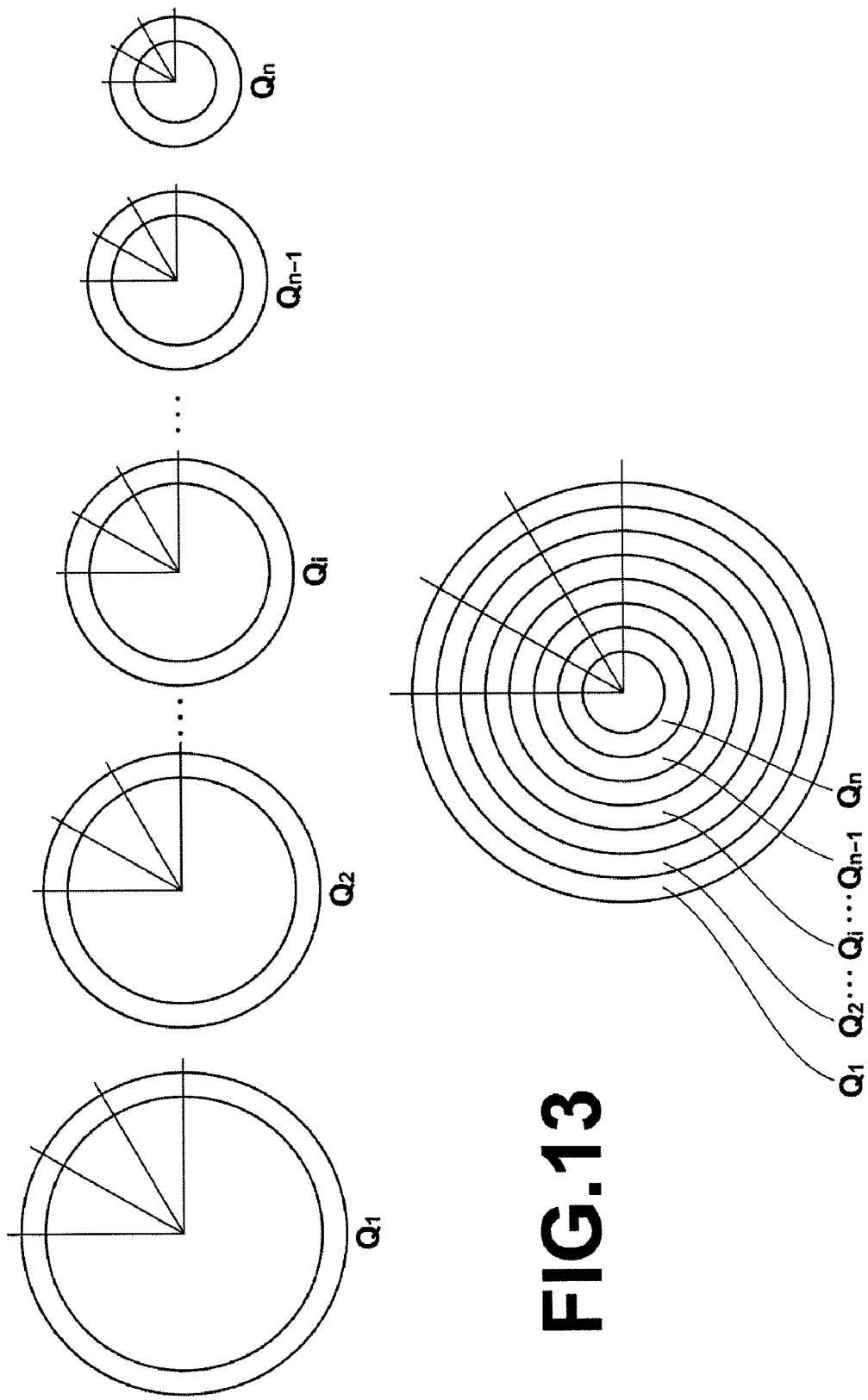
FIG. 13 is a drawing for explaining a conventional bull's eye display.

Still further, the description has been made of a case in which morphologies and functions of slice planes traversing the major axis are displayed in equal interval concentric circles as morphological and functional images. But, as shown in FIG. 11B, values of functional and morphological images may be disposed in relation to the distances of lines $S_1$, $S_2$, $S_3$, and $S_4$ radially extending along the surface of a heart as shown in FIG. 11A, whereby a bull's eye display dependent on the distances of surface shapes becomes possible. The bull's eye display dependent on the distances of surface shapes may provide an image like that shown in FIG. 12.

Further, the bull's eye display in which images located near the cardiac base are displayed near the center of the concentric circles and images located near the cardiac apex are displayed on the outer side of the concentric circles has been described. But, as in the conventional method, a bull's eye display in which images located near the cardiac apex are displayed near the center of the concentric circles and images located near the cardiac base are displayed on the outer side of the concentric circles is also possible.

Figure 14:
FIG. 14 shows an example of image including a morphological image and a functional image superimposed on top of each other (part 2).

In FIG. 9, the description has been made of a case in which the heart range represented by morphological image 210 and the heart range represented by functional image 200 are substantially the same. But, as shown in FIG. 14, the range of the blood vessel depicted in morphological image 210 may be wider than the range of the functions on the heart represented by functional image 200. The wider range of the heart represented by morphological image 210 than that represented by functional image 200 may provide a portion in which the anatomical position of the heart can be confirmed without being restricted by the display area of functional image 200 when morphological image 210 and functional image 200 are displayed in a superimposing manner, thereby facilitating understanding of the correspondence between the position and function of the heart.

FIG. 14 shows a case in which morphological image 210 outside of the concentric circles is wider than functional image 200. But morphological image inside of the concentric circles may be wider than functional image 200. Further, morphological image 210 both in inside and outside of the concentric circles may be wider than functional image 200.

As described in detail above, superimposition of a morphological image representing the morphology of a blood vessel, such as a coronary artery, on a functional image of a heart in bull's eye representation allows a comparative observation between the position and function of the heart.

What is claimed is:

1. A cardiac function display apparatus, comprising:
   a functional image generation unit for generating a functional image representing a function of a heart in each position using first voxel data of a three-dimensional medical image obtained by photographing a subject;
   a morphological image generation unit for generating, using a portion of second voxel data of a three-dimensional medical image obtained by photographing the subject, which are identical to or different from the first voxel data, corresponding to an area which includes a blood vessel along an outer myocardial wall of the heart, a morphological image depicting morphology of the blood vessel; and
   a superimpose display unit for displaying the functional image and the morphological image in a superimposing manner such that each position of the heart in the functional image corresponds to each position of the heart in the morphological image, wherein:
   the functional image is an image in which images representing functions of the heart on a plurality of slice planes cut in a direction traversing a major axis extending from a cardiac base toward a cardiac apex of the heart are arranged concentrically, and
   an image representing a function of the heart on a slice plane near the cardiac base of the heart is disposed near the center of the concentrically arranged images and an image representing a function of the heart on a slice plane closer to the cardiac apex of the heart is disposed in a position farther away from the center.

2. The cardiac function display apparatus of claim 1, wherein the morphological image is an image generated by performing MIP processing on voxel data present within a predetermined distance from the outer myocardial wall of the heart, which includes the blood vessel along the outer myocardial wall, and a blood vessel present in the predetermined distance is projected in the image.

3. The cardiac function display apparatus of claim 1, wherein the range of the blood vessel on the heart depicted in the morphological image is wider than the range of the functions of the heart represented by the functional image.

4. The cardiac function display apparatus of claim 2, wherein the range of the blood vessel on the heart depicted in the morphological image is wider than the range of the functions of the heart represented by the functional image.

5. A cardiac function display method performed by a cardiac function display apparatus, comprising:
   a functional image generation step for generating a functional image representing a function of a heart in each position using first voxel data of a three-dimensional medical image obtained by photographing a subject;

a morphological image generation step for generating, using a portion of second voxel data of a three-dimensional medical image obtained by photographing the subject, which are identical to or different from the first voxel data, corresponding to an area which includes a blood vessel along an outer myocardial wall of the heart, a morphological image depicting morphology of the blood vessel, including a width of the blood vessel, and morphology of a tissue along the outer myocardial wall other than the blood vessel; and a superimpose display step for displaying the functional image and the morphological image in a superimposing manner such that each position of the heart in the functional image corresponds to each position of the heart in the morphological image, wherein:

the functional image is an image in which images representing functions of the heart on a plurality of slice planes cut in a direction traversing a major axis extending from a cardiac base toward a cardiac apex of the heart are arranged concentrically, and an image representing a function of the heart on a slice plane near the cardiac base of the heart is disposed near the center of the concentrically arranged images and an image representing a function of the heart on a slice plane closer to the cardiac apex of the heart is disposed in a position farther away from the center.

6. A computer readable recording medium on which is recorded a program for causing a computer to function as:

a functional image generation unit for generating a functional image representing a function of a heart in each position using first voxel data of a three-dimensional medical image obtained by photographing a subject;

a morphological image generation unit for generating, using a portion of second voxel data of a three-dimensional medical image obtained by photographing the subject, which are identical to or different from the first voxel data, corresponding to an area which includes a blood vessel along an outer myocardial wall of the heart, a morphological image depicting morphology of the blood vessel; and a superimpose display unit for displaying the functional image and the morphological image in a superimposing manner such that each position of the heart in the functional image corresponds to each position of the heart in the morphological image, wherein:

the functional image is an image in which images representing functions of the heart on a plurality of slice planes cut in a direction traversing a major axis extending from a cardiac base toward a cardiac apex of the heart are arranged concentrically, and an image representing a function of the heart on a slice plane near the cardiac base of the heart is disposed near the center of the concentrically arranged images and an image representing a function of the heart on a slice plane closer to the cardiac apex of the heart is disposed in a position farther away from the center.

* * * * *